(12) United States Patent
Dimitrakos et al.

(10) Patent No.: US 9,195,852 B2
(45) Date of Patent: Nov. 24, 2015

(54) DISTRIBUTED COMPUTING SYSTEM

(75) Inventors: Theo Dimitrakos, Ipswich (GB); Srijith Krishnan Nair, Amsterdam (NL); Gabriela Gheorghe, Schuttrange (LU); Bruno Crispo, Trenot (IT)

(73) Assignee: British Telecommunications PLC, London (GB)

( * ) Notice: Subject to any disclaimer, the term of this patent is extended or adjusted under 35 U.S.C. 154(b) by 0 days.

(21) Appl. No.: 14/234,931

(22) PCT Filed: Jul. 27, 2012

(86) PCT No.: PCT/GB2012/000619
§ 371 (c)(1),
(2), (4) Date: Jan. 24, 2014

(87) PCT Pub. No.: WO2013/017815
PCT Pub. Date: Feb. 7, 2013

(65) Prior Publication Data
US 2014/0173687 A1  Jun. 19, 2014

(30) Foreign Application Priority Data

Jul. 29, 2011  (EP) .................................... 11250684

(51) Int. Cl.
*H04L 29/06* (2006.01)
*G06F 21/62* (2013.01)
*G06Q 10/10* (2012.01)
(Continued)

(52) U.S. Cl.
CPC .......... *G06F 21/6245* (2013.01); *G06F 19/322* (2013.01); *G06Q 10/10* (2013.01); *G06Q 50/22* (2013.01)

(58) Field of Classification Search
CPC ..... H04L 63/20; H04L 63/0227; H04L 63/10; H04L 63/1425
See application file for complete search history.

(56) References Cited

U.S. PATENT DOCUMENTS

| 6,505,244 B1 | 1/2003 | Natarajan et al. |
| 7,587,718 B1 | 9/2009 | Mincarelli et al. |

(Continued)

FOREIGN PATENT DOCUMENTS

| WO | WO 2008/101114 | 8/2008 |
| WO | WO 2009/039230 | 3/2009 |

OTHER PUBLICATIONS

International Search Report for PCT/GB2012/000619 mailed Oct. 17, 2012.

*Primary Examiner* — Izunna Okeke
(74) *Attorney, Agent, or Firm* — Nixon & Vanderhye PC

(57) ABSTRACT

A Policy Enforcement Point (PEP) enforcement module (100) comprises: a monitor (110), (120, 130, 140) for monitoring the output of a policy controlled module or PEP (200) operating within a distributed computer system and a correction performer module (150). The PEP (200) is associated with one or more policies (400) which are applied to the PEP. Each policy specifies a trigger event or events and an action or actions to be performed as a result of the trigger event occurring as well as expected output from the PEP (200) when it performs a specified action or actions. The monitor monitors output produced by the PEP (200) as a result of operating in compliance with a policy, and it compares the monitored output with one or more specified expected outputs specified in the policy. In the event that the comparison indicates a divergence between the expected and observed outputs a correction evaluator (140) evaluates an appropriate corrective action to take and issues a request to the correction performer module to perform such corrective action. The correction performer module (150) then performs the corrective actions as specified by the correction evaluator (140).

13 Claims, 7 Drawing Sheets

(51) Int. Cl.
　　*G06Q 50/22*　　(2012.01)
　　*G06F 19/00*　　(2011.01)

(56) References Cited

U.S. PATENT DOCUMENTS

2004/0098610 A1　5/2004　Hrastar
2004/0111725 A1　6/2004　Srinivasan et al.
2004/0193912 A1*　9/2004　Li et al. .................... 713/200
2008/0270438 A1　10/2008　Aronson et al.
2009/0080408 A1　3/2009　Natoli et al.
2010/0064184 A1　3/2010　Almeida et al.
2010/0070306 A1　3/2010　Dvorak et al.
2010/0119131 A1　5/2010　Gebow
2011/0119309 A1　5/2011　Aronson et al.

* cited by examiner

```
<x-ray>
    <patient>
        <id>123<//>
        <lastname>Jones<//>
    <firstname>Danny<//>
    </patient>
    <diagnosis>abdominal pain</ diagnosis >
    <width>2048</ width >
    <height>2500</ height >
    <bit-depth>16</ bit-depth >
</x-ray>
```

Figure 4

```
<x-ray>
    <patient>
        <id>123<//>
        <lastname>xxxxx<//>
    <firstname>xxxxx<//>
    </patient>
    <diagnosis>abdominal pain</ diagnosis >
    <width>2048</ width >
    <height>2500</ height >
    <bit-depth>16</ bit-depth >
</x-ray>
```

Figure 5

```
<AuditEntry timeStamp="1275583457352"
messageID="Id-00000128feb2e848-00000000002b452b-1520"
level="Success">
<clientIPAddr>127.0.0.1</clientIPAddr>
<filterName>Log Before</filterName>
<filterType>LogMessagePayloadFilter</filterType>
<logText>'LogBefore' logged msg payload</logText>
</AuditEntry>
<payload>
<![CDATA[
--- HTTP method data here
--- soap envelope here ]]>
</payload>
```

Figure 8

```
String q = new String(
"declare namespace soapenv =
\"http://schemas.xmlsoap.org/soap/envelope/\";"
+ "declare namespace " + rc.getTagXmlns()
+ "=\"" + rc.getXmlns() + "\";"
+ "/soapenv:Envelope/soapenv:Body/"
+ rc.getRelevantTag());
Nodes res=new XQuery(q,null).execute(doc,null,null)
.toNodes();
```

Figure 9

```
"/soapenv:Envelope/soapenv:Body/"+tagPacientData
+ "[lucene:match(.," + anonymousValue() + ")>"
+ similarityScore + "]"
```

Figure 10

DISTRIBUTED COMPUTING SYSTEM

This application is the U.S. national phase of International Application No. PCT/GB2012/000619 filed 27 Jul. 2012 which designated the U.S. and claims priority to EP 11250684.5 filed 29 Jul. 2011, the entire contents of each of which are hereby incorporated by reference.

TECHNICAL FIELD

The present invention in certain example embodiments relates to a distributed computing system and in particular to a method and apparatus for automatically monitoring policy enforcement within a policy driven computer system operating in a service-oriented architecture and preferably also for correcting any policy enforcement behavior determined as being incorrect.

BACKGROUND AND SUMMARY

Policy driven approaches to managing distributed computing systems, especially for managing security aspects of such systems, are becoming increasingly popular. An important factor in this popularity may well be the ease with which such policies can be understood by human administrators. A typical way for a policy driven system to be implemented is to have one or more Policy Decision Points (PDPs) and one or more Policy Enforcement Points (PEPs). The PDP's simply need to be able to observe properties of the system which they are controlling and which are pertinent to the set of policies about which they need to make decisions. The PEPs are devices which carry out actions determined by a PDP. Thus for example, a policy might specify that patient records to be transmitted to an external device should be anonymization by having' the patient name field set to a default value such as "XXXX". A PDP might then inspect all outbound messages en route to a message sending device (e.g. a gateway router having access to external network addresses). If the PDP observes an outbound message en route to the message sending device that includes a patient record, it can send an action request to instruct the message sending device (which would thus be the PEP) to first anonymize the patient name field before sending out the message in question to an external network.

Another important development in computing in recent years is the trend towards what is often referred to as a Service-Oriented Architecture. In this general approach; computing functionality is provided as a service which is available via a network connection with messages being passed between a client device (acting as a consumer of a service) and a server device (acting as a service provider). SOA also refers to ways in which consumers of services, such as web-based applications, can be made aware of available SOA-based services. For example, several disparate departments within a company may develop and deploy SOA services in different implementation languages and their respective clients can benefit from a well understood, well defined interface to access the services. EXtensible Mark up Language (XML) is commonly used for interfacing with SOA services (i.e. messages passed between services and their clients are written in XML).

According to a first aspect of the present invention, there is provided apparatus for use as a device within a distributed computing system, the distributed computer system comprising a plurality of devices interconnected by a data network such that each of the interconnected devices can communicate with each other using messages transmitted over the data network, wherein the apparatus comprises: a monitoring component and a correction component; wherein the monitoring component is operable to monitor the output of a policy controlled device, the policy controlled device forming one of the devices of the distributed computer system, the policy controlled device being associated with one or more policies which are applied to the policy controlled device in order to control the behavior of the policy controlled device, the or each applied policy specifying a trigger event or events and an action or actions to be performed by the policy controlled device as a result of the trigger event being detected as having occurred, the monitoring component being operable to monitor output produced by the policy controlled device (especially output generated as a result of a detection having been made of a triggering event or events specified within one of one or more applied policies); and the monitor being further operable to compare the monitored output with one or more specified expected outputs and to generate a correction request in the event that the comparison indicates a divergence between the expected and observed outputs; and wherein the correction component is operable to perform corrective actions as specified in the correction request generated by the monitoring component.

Preferably the correction component is not the policy controlled device/module. Furthermore, the corrective actions preferably do not include making any kind of modification to the policies associated with the policy controlled device (or module). The significance of these two preferred features is discussed in greater detail below. Preferably the policy controlled device/module is a Policy Enforcement Point (PEP) within the meaning of this term as used within the various documents defining and describing the Common Open Policy Service (COPS) protocol (such as the IETF documents RFC 2748 and RFC 3084). Policy based decisions may be made either by a Policy Decision Point (PDP) as this term is used for COPS purposes or by the policy controlled module.

The terms "device" and "module" may be used in a largely interchangeable manner throughout this specification since, generally speaking, the behavior of a device on the network will be mostly determined by software running on the device. Thus the device will behave in a manner which is largely specified by the software which is running on it at any given time. The term "module" is generally used to refer to a piece of software which can be considered as being somewhat self-contained. A particular module may well dictate the behavior of the device on which it is running at any given time for the purposes of the present application. Given the interrelated nature therefore of a device and the software running on it at any given time it is self-evident that the terms from a practical perspective may in many situations be used interchangeably. Of course, a single device may have several software modules running thereon simultaneously at any given point in time, however, this does not affect the interchangeability of the terms in many circumstances where the behavior of a device of interest is largely affected by merely a single software module at any given point of time of interest.

Monitoring (e.g. as performed by the claimed monitoring component) is generally simply a case of receiving and analysing data output by the policy controlled device (or module) (which may, for example, be a PEP); the output data may be either the direct output of the device (e.g. messages being transmitted to another device in the distributed computer system) or log data (generally devices (or modules) in a distributed computer system are likely to generate log data if requested to do so by a system administrator). However, in theory the monitoring could take an altogether different form—for example if the monitored device performed some sort of mechanical function (which would then constitute the "output" of the policy controlled device) the operation of the device could be observed by a suitable measuring/observing device (e.g. a camera) and the output of this measuring/observing device, could then be fed back to the monitoring component as input data to the monitoring component etc.

Preferably the policy controlled module is operating within a Service Oriented Architecture (SOA) and the outputs of the policy controlled module/device are messages (most preferably XML based messages and/or SOAP messages (SOAP being the W3C organization's protocol that originally stood for Simple Object Access Protocol)).

Thus, preferred embodiments of the present invention mitigate the problem of PEP devices/modules (especially those operating within a Service Oriented Architecture) implementing action requests (e.g. as sent from a PDP) incorrectly, by monitoring the outputs of PEP devices/modules and checking to see if those outputs agree with expected outputs, and by correcting wrong outputs automatically (preferably without modifying the PEP in question or any policies relevant to the operation of the PEP).

As mentioned above, preferably, the correction apparatus is not the policy controlled device/module. The point of this is that the policy controlled module may be a complex third party piece of software (or a device running such a piece of software) the internal operation of which is unknown to the administrator of the computer system who is in charge of monitoring the overall system behavior. As a consequence of this, it is not clear that it will correctly perform the desired corrective action. It is therefore easier to use an alternative module which can have been created simply for the purpose of performing such corrective actions when necessary. This corrective module (or correction component) can be entirely controlled and well understood by the system administrator unlike the policy controlled module being monitored. Similarly, contrary to some known feedback mechanisms for implementing policy driven control over network devices (e.g. see U.S. Pat. No. 6,505,244), it is preferred if the policies themselves are not altered by the corrective action. The point here is that there is a difference between a correct policy being implemented incorrectly and an incorrect policy causing undesirable actions. The present invention in certain example embodiments is concerned with the former problem. If it is successfully detected that a policy is being incorrectly implemented by a PEP then simply changing the policy could have undesirable and unpredictable effects. It is better to correct the outputs in such a situation than changing the inputs (e.g. the policy).

As a simple example to illustrate how this might work in practice, one can consider a scenario in which an online shop has a web-server which once a customer has placed an order that s/he wishes to finalize by making payment using a credit or debit card, the web-server redirects the user to a secure web-payment service. Using PDP and PEP notation, one can view the web-server as being, or including, a PDP which determines when sufficient trigger "events" have occurred (e.g. filling up a virtual shopping cart and pressing the pay now button or something similar) to trigger a request to be sent to a corresponding secure web-payment service which can thus be viewed as a PEP (or as a policy controlled device according to the terminology used in the claims of the present application). In most cases (say more than 95% of the time for example) one would expect such payments to be successful. This expectation could be formalized as an expected output from the policy controlled device. If a large number of failures started to occur, the system could try to take corrective action, e.g. by automatically redirecting customers to a different secure web-payment service.

An important point to note which is illustrated by the above example is that the expected output might not relate directly to the actual processing performed by the PEP. i.e. it is not necessary to know for certain what the correct outcome should be for a particular customer (and thus it is not necessary to be able to recreate the processing that the policy controlled document should have been performing), it is enough to know that because too many customers are failing to make payment successfully there is probably some fault with the policy controlled device (the secure web-payment service). Alternative examples of expected outputs might be an expected correlation between two kinds of results from a PEP, or correlations of outputs from distinct policy controlled devices or from one policy controlled device and some other device, or other indirect indications that the PEP is performing incorrectly in some way. Another important point to note is that in many practical situations, the corrective action which is taken is simply to substitute one policy controlled device for another which offers the same or equivalent services. This is particularly applicable in a service oriented architecture environment in which there are likely to be several competing and generally interchangeable service providers for any given service. One useful way in which embodiments of the present invention can thus be used is to enable a cheaper but less reliable service to be used most of the time with an option to revert to a more expensive but more reliable alternative only where the cheaper service is observed to be behaving in a manner which suggests it is behaving incorrectly.

In a preferred embodiment, there is provided a computer system comprising:
  a number of computer components whose behavior may be specified at least in part by one or more policies;
  a plurality of policy enforcement points; and
  a policy enforcement point monitor which monitors one or more of the policy enforcement points; wherein each policy enforcement point includes:
  a polity store for storing policies which relate to the controlled components; an event driven engine for receiving information about events which occur in the system, assessing if any of these events is a trigger for one of the stored policies in respect of one of the controlled components and for taking an action when necessary based on the triggered policy;
  a trace generator for storing information about actions taken by the policy enforcement point; and
  a policy enforcement point compensation engine for carrying out compensation actions in accordance with instructions from the policy enforcement point monitor; and wherein the policy enforcement point monitor comprises:
  a store for storing assessment policies, each of which is associated with a policy or policies stored by policy enforcement point monitored by the policy enforcement point monitor and comprises information specifying criteria which can be used to assess whether or not the or each associated policy has been correctly carried out by the associated policy enforcement point;
  a trace analyser for analysing information generated by the trace generator of a monitored policy enforcement point together with an associated assessment policy to assess the extent to which actions taken by the policy enforcement point have been correctly carried out in accordance with the associated policy stored by the respective policy enforcement point; and a policy enforcement point compensation engine instructor for instructing the policy enforcement point compensation engine of the monitored policy enforcement point to automatically carry out compensatory actions as specified in the respective assessment policy in the event that it is determined to be appropriate to do so as a result of analysis performed by the trace analyser.

According to a second aspect of the present embodiment, there is provided a method comprising: monitoring the output of a policy controlled module, operating within a distributed computer system, the policy controlled module performing one or more actions resulting in some output in response to a decision taken based on the detection of an event which triggers a pertinent policy associated with the policy controlled module; comparing the output of the policy controlled module with one or more specified expected outputs and generating a request for corrective actions in the event that the comparison indicates a divergence between the expected and observed outputs; and performing corrective actions in accordance with the generated request for corrective actions.

Preferably, performing corrective actions comprises one or more of: modifying the output of, or the input to, the policy controlled module or modifying the behavior of the policy controlled module without modifying a policy applied to the policy controlled module.

Embodiments of the present invention provide an architectural framework with three main aims:

to dynamically assess the correctness of the enforcement of a policy in a distributed setting with a shared infrastructure;

to automatically correlate the violations of the enforcement mechanisms with appropriate corrective actions; and to perform the corrective actions that have been identified by the above mentioned correlation.

An advantage of such a framework is that it provides a quantitative measure of the level of compliance of a runtime system, and helps its appropriate adaptation. In preferred implementations, this is done by analyzing relatively low-level messages between service providers and service consumers as well as by matching deviations from desired behavior with certain correlated corrective actions.

This framework is applicable in very generic scenarios where the infrastructure or parts of it are shared among several participants (Web service providers and consumers). In such cases, it is essential for both the owner of the infrastructure and its clients to know that there are entities who are misbehaving with respect to known constraints, as well as to have the system dynamically/automatically correct these flaws as soon as they are detected. In the present application, the term "infrastructure," as used above refers to the middleware that realizes all the communication requirements of an entity (e.g. a computer sub-system which consumes Web services or an entity which offers such a web service) deployed in a Service-Oriented Architecture manner. The communication among any such entities is therefore mediated by this infrastructure.

This framework gives a practical and quantitative assessment of how well infrastructural policy constraints are complied with. This is useful and (re)usable for all parties involved in running a Service Oriented Architecture (SOA) application: service providers, service clients, infrastructure providers and users. For example, whenever two parties establish a provision or usage agreement such as a Service Level Agreement (SLA), there needs to be some sort of evaluation of how the contractors fulfil fulfill their promises. The criteria to evaluate the deviation from the expected compliance, level are mostly business dependent, but embodiments of the present invention support customization in two important respects: first, the monitor may be supplied with customized descriptions of the misbehaviors (or policy violations) that have the biggest impact on the application. This is feasible since security administrators usually know what these damaging misbehaviors are. Secondly, the quantified damage of such potential misbehaviors can also be customized by the user. Along this process of assessment, the infrastructure providers can know how many of their constraints are not satisfied by the infrastructure users. Additionally, the infrastructure users know how noncompliant they are. Also, service providers can get a clear idea about how many and what kind of misbehaving clients they have (this happens when their constraints on service usage are defined and enforced at the infrastructure level).

Further aspects of the present invention relate to computer programs for carrying out the methods of the invention and to carriers, most preferably non-transient computer readable media carriers (e.g. magnetic or optical disks (e.g. hard-drives, CD's DVD's etc.), non-volatile solid-state memory devices (e.g. solid-state drives, usb thumb-drives, etc.), volatile solid-state memory devices (e.g. DRAM modules, etc.), etc.), carrying such programs.

BRIEF DESCRIPTION OF THE FIGURES

In order that the present invention may be better understood, embodiments thereof will now be described, by way of example only, with reference to the accompanying drawings in which:

FIG. 4 is a schematic illustration of an extract from an example XML patient record before anonymization;

FIG. 5 is a schematic illustration of the extract from an example XML patient record shown in FIG. 4 after anonymization has been performed on the record;

FIG. 8 is a schematic illustration of an XML record of a log event generated by the PEP of FIG. 2 when implemented according to the Vordel enforcement blocks of FIG. 7;

FIG. 9 is a schematic illustration of a portion of java code used to execute an XML query on a file of log entries of the type illustrated in FIG. 8; and FIG. 10 illustrates a modification to the code of FIG. 8 to generate match scores on records identified by the query of FIG. 9.

DETAILED DESCRIPTION OF EMBODIMENTS

Figure 1:
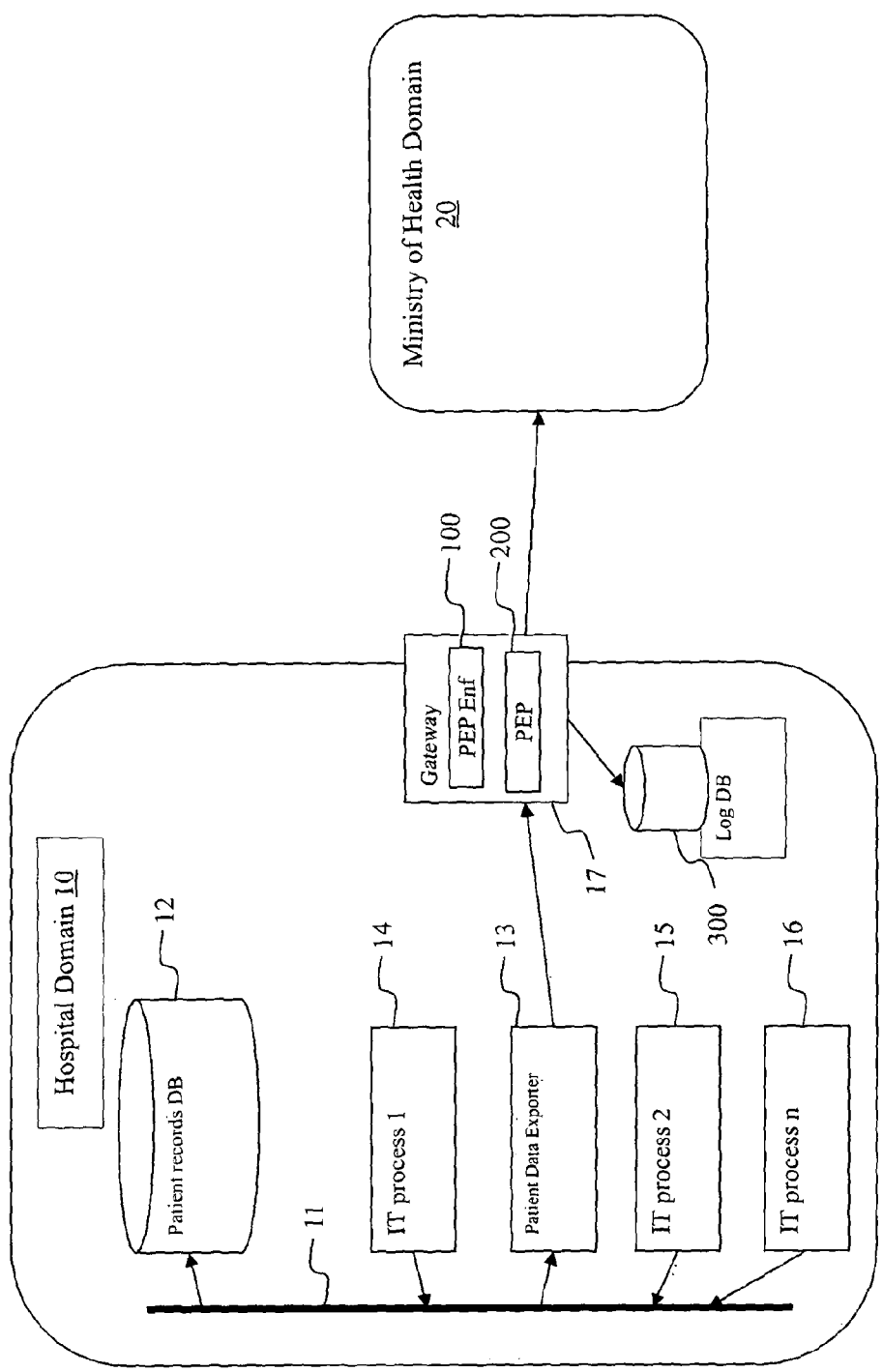
FIG. 1 is a schematic overview of a first embodiment of the present invention.

A first embodiment concerns a hospital setup as shown schematically in FIG. 1. In this setup the hospital has a number of computers and databases etc. within its domain 10 connected together via a network implementing a message bus 11. The hospital keeps data records of all its patients within a patient records database 12 and is required to periodically report some of the data to the Ministry of Health for both statistical and payment-related reasons. It does this via a patient data exporter service 13 which runs as a service on a server computer operating within the hospital's domain. The Ministry of Health requires several categories of data—doctors' activity in terms of patient cases that were handled, surgery data, hospitalized cases, drug administered etc. Such reports are produced at the hospital side by several different IT services (14, 15, 16, etc.), and they all relate to patient data. In the light of privacy regulations, the reports must be anonymized of all sensitive patient data, but at the same time, some patient data must remain in the record so as an audit of the hospital system could track individual activities related to patients without their private data being disclosed. In order to have a flexible way of implementing anonymization services for the variety of IT services (e.g. services 14, 15, etc.), and to connect easily with its contractors, it was decided that the hospital infrastructure would use a message bus 11 operating over the network and also that it would implement the system in a phased manner.

The present embodiment concerns the first phase implementation relevant to year one of the project. As shown in FIG. 1, the implementation of the anonymization process is done internally (i.e. within the Hospitals domain 10) by means of a gateway 17 through which data exported by the patient data exporter 13 is sent to a server located in the Ministry of Health's Domain 20. Associated with the gateway 17 is a log database 300 in which log information from the gateway is stored. The hospital's security administrators in this embodiment use their own internally developed privacy enforcing process (operating as a Policy Enforcement Point (PEP) 200 running on the gateway 17) such that all data that is expected to exit the hospital system, from different reporting services, will go through the same gateway point 17 (including PEP 200) where the sensitive parts are inspected and filtered out. For a yearly compliance audit on data security, the hospital needs to know how well their patient data anonymization works and whether any sensitive information has been leaked.

In addition, in the present embodiment this process is bolstered in accordance with the present invention by additionally monitoring in close to real time all actions taken by the PEP 200 to ensure that the PEP is correctly enforcing the policy requirement (of anonymising all patient record data which is exported to the Ministry of Health Domain 20): The entity which monitors the PEP is the PEP enforcer 100 which, in the present embodiment also runs on the gateway 17.

In the present embodiment, the gateway 17 is formed by means of a conventional server computer running a gateway software application which receives, processes and then forwards on to devices outside the Hospital Domain 10, messages in the form of SOAP messages received from applications running within the Hospital Domain 10 (in particular from the Patient Data Exporter 13). The PEP, enforcer 100 is provided as software which, in the present embodiment, is generated by a software tool provided by a company called Vordel. This software tool includes user configuration software which permits the PEP gateway software to be configured by an administrator for example to specify the destination device for received SOAP messages based for example on the specified destination of the received SOAP message etc. Additionally, the configuration software permits an administrator to specify filter functions, etc., which are discussed in greater detail below.

Figure 2:
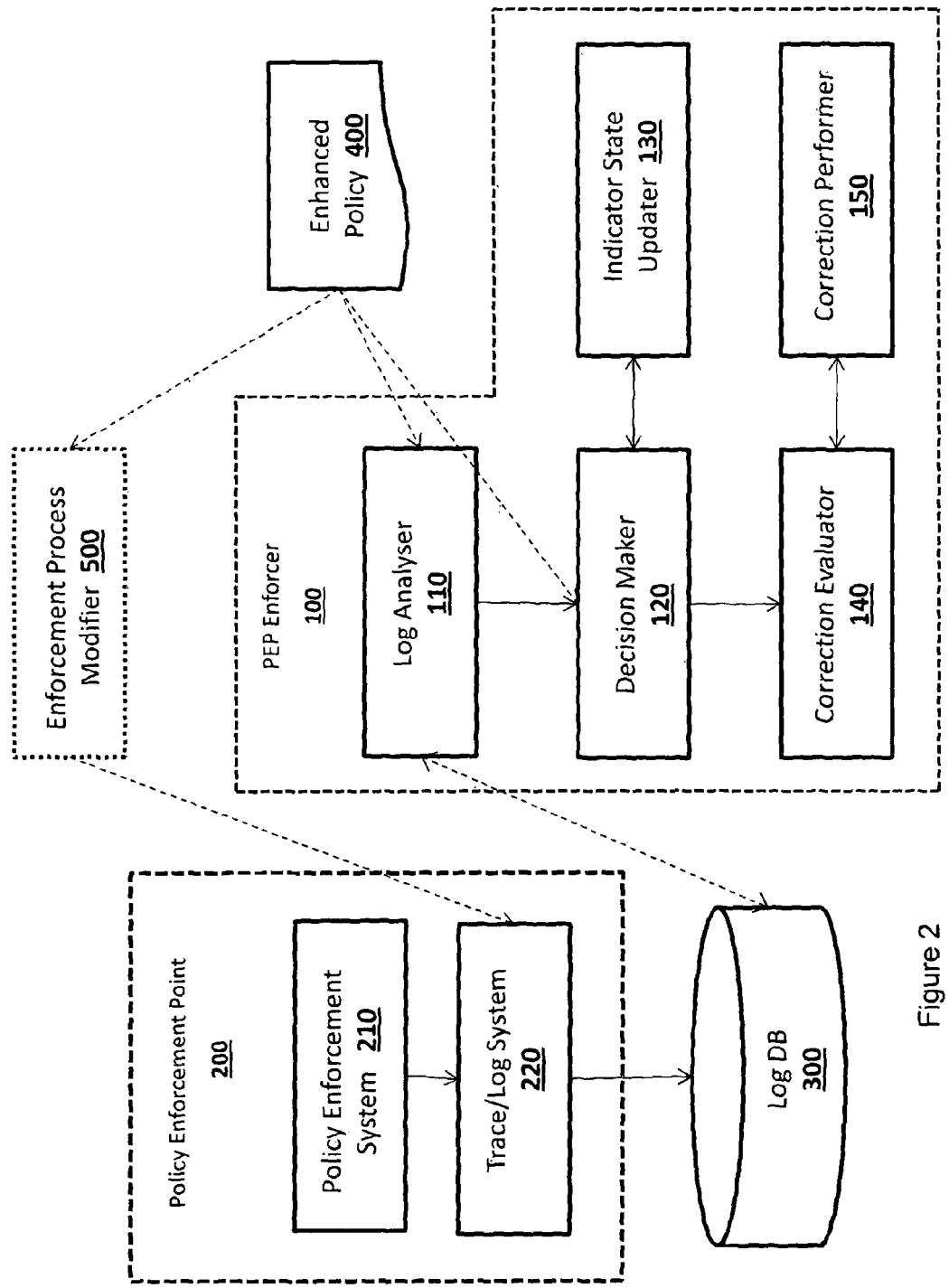
FIG. 2 is a block diagram of the functional modules forming a Policy Enforcement Point (PEP) and a PEP Enforcer, both running on the gateway shown in FIG. 1.

FIG. 2 illustrates in overview the functional modules of the PEP 200 and the PEP enforcer 100 of the present embodiment. In addition to the PEP enforcer 100 and the PEP 200 itself, FIG. 2 also illustrates the log database 300 in which log data from the gateway 17 (and particularly from the PEP 200) is stored as well as an enhanced policy 400 (which in this embodiment takes the form of an XML record having a similar format to a conventional XML policy for controlling a PEP such as PEP 200).

The PEP 200 comprises a policy enforcement system functional module 210 which is responsible for carrying out the required actions specified by the appropriate policy whenever a trigger of that policy occurs. In the present example, it is responsible for performing an anonymisation (action) on all received SOAP messages which contain patient records and which are destined for the Ministry of Health (condition). Additionally, the PEP 200 includes a Trace/Log system 220 which is responsible for storing some kind of trace of the actions which the policy enforcement module performs—typically in the form of some kind of log data stored in a log database or just in a log file somewhere etc. In the present embodiment, the log data is stored within a Log DataBase, Log DB 300.

The PEP Enforcer 100 of the present embodiment comprises five key functional modules. These include a Log Analyser 110 which is responsible for parsing the contents of the log DB 300 to look for data (e.g. records) which could potentially indicate that the PEP 200 has failed to correctly implement a particular policy (e.g. enhanced policy 400 discussed below); such data/records are referred to as potential violation data/records. The PEP enforcer 100 additionally includes a Decision Maker functional module 120 which receives the potential violation data/records and examines them to see if they are in fact indicative of a violation of the policy by the policy enforcement point PEP 200; it also, in the present embodiment, determines an extent of the violation (in the present example as a score which is a number between 0 and 1 where 1 represents no violation and 0 represents maximum violation attributable to a single violation record). The PEP enforcer 100 additionally includes an Indicator State Updater 130 which is operable to update the value of an indicator based on information received from the Decision Maker module 120; in the present embodiment it receives scores from the Decision Maker in respect of each potential violation record and uses these to update an indicator value; in the present example this is done (by the Indicator State Updater 130) by adjusting the indicator value according to the following equation:

$$\text{(new) Indicator Value} = a*(\text{old) Indicator Value} + b*\text{score}$$

where, in the present case, a=0.8 and b=0.2 (though a and b can generally take any values between 0 and 1 such that a+b=1, where the greater a is, the less significance a single score has on the updated indicator value); furthermore it should be noted that in alternative embodiments an equation to use for updating the indicator value could be specified in an enhanced policy and this equation could then be automatically extracted from the enhanced policy by the Indicator State Updater and used—the above equation could also be kept as a default equation in such a case for times when the enhanced policy omits to include a specific equation to use instead of the default. The Decision Maker 120 monitors the Indicator value and informs a fourth functional module of the PEP Enforcer 100, the Correction Evaluator functional module 140, if the indicator value satisfies some predetermined condition; in the present example it notifies the Correction Evaluator 140 if the indicator value goes below 0.7, but any value can be used here depending upon the severity of the violation being monitored for, etc. Finally, the PEP Enforcer 100 additionally includes a Correction Performer functional module 150 which is actually responsible for carrying out the correction. In the present embodiment, this is done by replacing some of the code used in the PEP 200 with alternative code, but the actual nature of the correction can take many different forms as discussed below.

FIG. 2 also illustrates an enhanced policy 400. This is discussed in greater detail below, but in the specific embodiment described in greater detail below, this specifies not only the policy which the PEP 200 is to enforce (e.g. anonymising patient records destined for the Ministry of Health), but also an indication of how violations of this policy can be detected (e.g. by the Levenstein distance between the detected value for a patients name field and the "correct" anonymised value of "XXXX"). In future more sophisticated embodiments, the enhanced policy could include enforcement process modifications. An example of these would be requirements for the PEP 200 to be modified to include specific logging capabilities. Such a future embodiment might include an additional optional functional module (perhaps also forming part of a modified PEP Enforcer 100) such as the illustrated Enforcement Process Modifier functional module 500 illustrated in dashed lines to indicate that this is only an optional module which might be included in future alternative embodiments. The Enforcement Process Modifier 500 would be operable to parse the Enhanced policy 400 and identify what changes need to be made to the PEP 200 (e.g. additional logging or other trace generating capabilities)—as well as to then cause such changes' to be made to the PEP 200.

Figure 3:
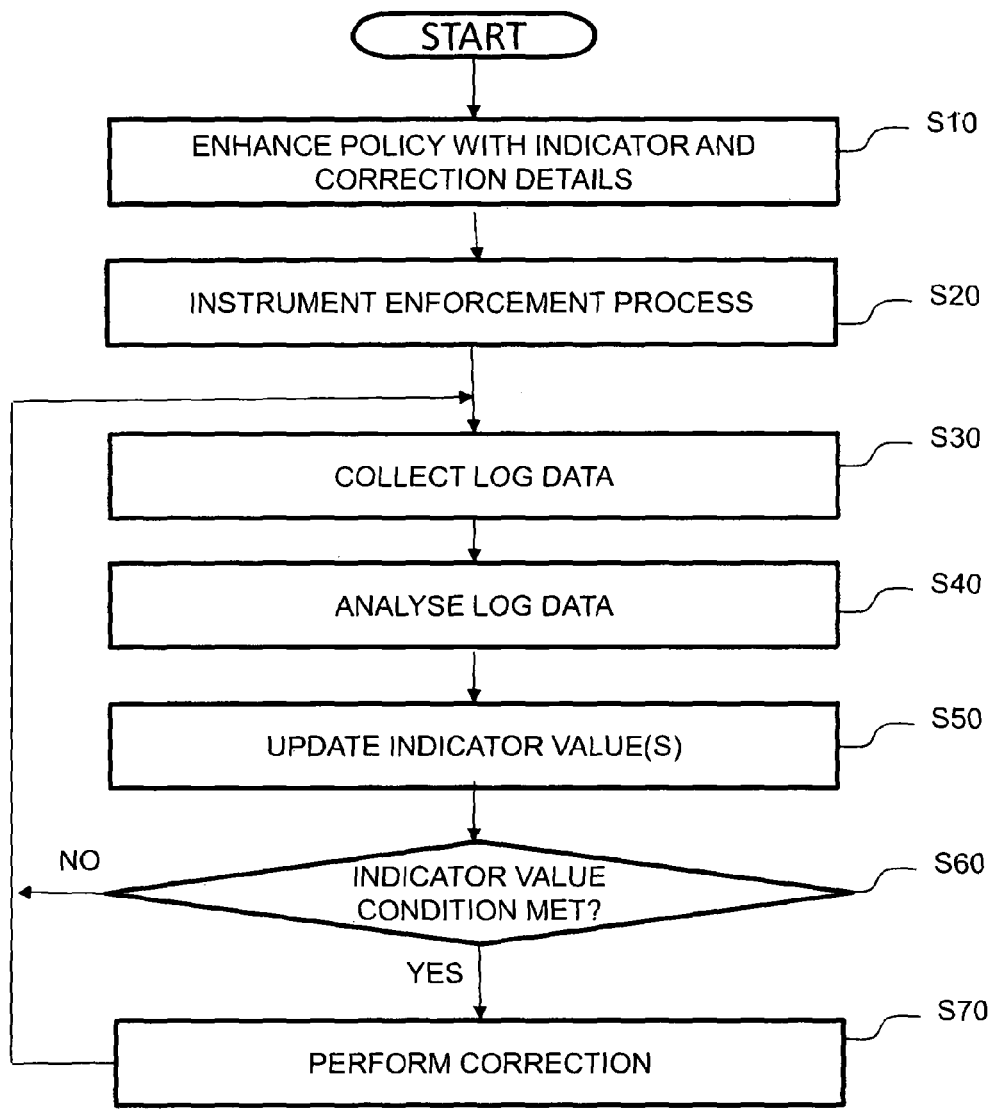
FIG. 3 is a schematic diagram illustrating the steps performed by the PEP and the PEP enforcer in order to implement an extended policy specifying both a policy to apply to the PEP for controlling the behavior of the PEP and processes for measuring the compliance of the PEP with the applied policy.

Turning now to FIG. 3, this shows in overview the steps performed by the various components of the system of FIG. 1 with particular reference to the PEP 200 and the PEP Enforcer 100. The overview includes some steps which are performed manually in the present embodiment and can therefore be thought of as happening prior to a method according to the present invention; in alternative future embodiments at least some of these manual steps may be automated and thus fall within the scope of the present invention.

Thus, upon commencement of the method at step S10, an enhanced policy is generated. This is typically done by a human administrator manually generating such a policy; in the present embodiment it is anticipated that such enhanced policies will be created by modifying an existing normal (i.e. not enhanced) policy to include details of what a policy violation would look like (including possibly how to detect and measure such a violation—especially the additional logging requirements that will be needed to detect such violations and the analysis that will need to be performed on the resulting log data) and possibly also details of how a correction should be made if such violations are detected.

Having generated an enhanced policy at step S10, the process proceeds to step S20 of modifying (or instrumenting) the PEP 200. In the present embodiment, this is done as a manual step by an administrator reading the enhanced policy and judiciously determining what extra logging or other trace capability should be added to the PEP 200 and then adding it. In alternative future embodiments this step could be automated—for example the enhanced policy could give explicit detail about the logging capabilities required and then an automated enforcement process modifier functional module could cause such capabilities to be added to the PEP. The actual sub-steps performed to carry out the modification/instrumentation of a PEP in a specific example are described with reference to the specific example given below.

Steps S10 and S20 may be considered preliminary steps which are performed before the system enters runtime (in which the PEP 200 is operational to carry out actions based on the enhanced policy (in particular the "normal" part of such policy)). Upon completion of step S20 the process therefore enters the runtime and this includes step S30 in which log data is collected by the PEP 200 (in particular the Trace/Log System 220 thereof) and stored in the Log DB 300.

Then, at step S40 the PEP enforcer 100 (in particular the Log Analyser 110 together with the Decision Maker 120 thereof) analyses the log data from the Log DB 300 and identifies potential violation records and assesses these.

Then at step S50 the results of the assessments performed in Step S40 are used (in particular by the indicator state updater 130) to update an indicator value or values. At a step S60, the indicator value is monitored and if it is determined (by the Decision Maker 120) that a condition associated with the indicator value has been met (e.g. if the value drops below a threshold value, etc.) then the method proceeds to step S70 in which an appropriate correction is determined (by the correction evaluator 140) and made (in particular by the correction performer 150). Once the correction has been performed the method loops back to step S30 to continue collecting log data. If no such condition is satisfied by the indicator value (e.g. it has not fallen below some predetermined threshold) then the method simply loops back to step S30 without first passing to step S70.

The data used to enhance the policy in step S10 may, in future embodiments, include:
1. possible violations that are most damaging to the system, and their accompanying gravity coefficient (this can be some simple weighting);
2. location indication of what parts of the enforcement process implementation are prone or more susceptible to such violations;
3. correction information, such as a particular correction to be performed, in the form of a suggestion (that is desirable and can correct the targeted misbehavior).

Such location pointers may, in future embodiments, be used in the next step S20—that of instrumenting the enforcement process such as to obtain log data exactly at those locations that are prone to be the sources of misbehavior (or flaws). With this information inserted in the enforcement process, the resulting customized log data is then collected (at step S30).

In the next step S40, the log data is analysed, in real-time as the system is executing. The assessment of the data in the logs is reflected in updating of an indicator value. If the indicator value, e.g., drops or rises above certain threshold values, the suggested corrections are enacted. The loop is closed by returning to the collection and analysis of the log data in step S30 and S40. This means that the corrected system will be reassessed (if/when a correction is performed).

In embodiments, the corrective actions can include, but are not limited to:
  raising an alarm;
  invoking a corrective Web service; or
  replacing an enforcement entity (e.g. a PEP), or a part thereof, or a group of enforcement entities (or mechanisms) without modifying the requirements of the policy.

Note here that corrections may (1) be delegated to external entities, or (2) modify the functioning the underlying enforcement controls, without changing the requirements of the policy.

As noted above, in order to react in a timely manner and to correct misbehaviors, the log data is analyzed on the fly. This log data, in the present embodiment, contains all message communications (SOAP messages) coming and going through a Web service endpoint, as well as the data about processing steps taken at the endpoint. Hence, at runtime, the Log Analyzer (LA) and to the Decision Maker (DM) use information (which may have been specified in and obtained from the enhanced policy) to determine what data is potentially relevant and the extent to which any potentially relevant data indicates a violation of a policy has occurred. The LA needs criteria to differentiate between relevant and non-relevant log entries (and this information may be provided by the enhanced policy) and forwards potentially relevant data to the Decision Maker (DM). The DM in its turn performs three kinds of actions:

1. communicating with the Indicator State Updater such that is can correctly update an indicator value,
2. deciding whether an indicator value has satisfied some predetermined condition (e.g. reaching or surpassing predefined thresholds defined in the enhanced policy), and therefore if it is time to perform some correction, and
3. matching the right correction with its causing misbehavior, and calling the Correction Evaluator (CE) with a set of appropriate parameters.

The Indicator State Updater (ISU) receives information from the DM about which indicators to update, and may, in some embodiments, output the current and past values of indicators to a system end-user.

The idea behind using Indicator States to indirectly decide the correction to be taken (instead of letting the presence of a certain event in the log trigger a specific correction) is to enable the flexibility to evaluate the severity of the violation events. For example, the presence of a specific log message once in a time period could mean a lower severity than its presence, say, twice in the same period. These two kinds of occurrences cart thus lead to different indicator values, furthermore, in refined embodiments, these could be further combined with indicator values calculated from the presence of other (types of) log messages to provide a cumulative indicator value that reflects the overall severity of the state of the enforcement system's deviation from its expected behavior. This then enables the Correction Evaluator to choose the appropriate correction to take at a very fine granular level.

The Correction Evaluator (CE) may receive parameters indicating correction process that it is supposed to trigger and if necessary, additionally parameters appropriate to that correction process (e.g. specifying properties specific to that correction process—e.g. if a portion of the PEP is to be replaced with new code the Correction Evaluator may receive parameters indicating that a portion of code associated with the PEP is to be replaced and parameters indicating which portion of code is to be replaced and what code is to replace it, etc.). In future embodiments the CE may be operable to match between coarser correction processes or more abstract workflows, and atomic correction actions to be delegated to the Correction Performer (CP). If, for instance, the correction is to trigger an alarm to both the police and system administrator, then the CE decides that the alarm consists of invoking two Web services, but it decides the order in which these calls be dispatched to the Correction Performer, and their accompanying parameters.

The Correction Performer (CP) is the executor for the primitives received from the CE. It is a software component that performs a correction (without needing to have prior knowledge of the exact context of the violation). It may be given a set of parameters specifying what correction is to be performed and it is in charge of executing a task; for example, in some embodiments When a correction requires the raising of an alarm, the CP may receive one or more parameters which specify the severity of the alarm, the entity to which the alarm is aimed (i.e. the entity to be notified by the alarm), the component or service to which the alarm relates, etc. An alarm could be, for example, an email message sent to the administrator of the system, or a specialized notification to a business manager. In such a case, the CP would include, for example, an email or SMS client, etc.

if the correction requires invoking a Web service or a software function, then the CP can be specialized for a certain emergency procedure: for example, shutting down or isolating a component where a violation was detected, limiting the communication of such a component with all its partner components, etc.

If the correction requires altering the policy parameters as a response to repeated violations, the CP may be operable to activate a third-party entity whose task would be to actively monitor the source of repeated violations, and to limit its communication links based on updated runtime parameters (which may be supplied by the CE, etc.).

If the system stores information specifying descriptions of different actions which may be performed by one or more correction performers, the CE in some embodiments can be arranged to use this information to map the correction capabilities of the known CPs with the correction needs requested by the DM.

Referring now to FIGS. 4 and 5, FIG. 4 illustrates an extract from an example XML patient record of the type which the present embodiment processes, prior to it being anonymised by the PEP 200. FIG. 5 shows the same extract after the record has been duly anonymised. It will be noted that the "lastname" and "firstname" fields (specified by the corresponding tags respectively) have been changed between FIGS. 4 and 5 from "Jones" and "Danny" respectively in FIG. 4 to "xxxxx" in FIG. 5.

In the present embodiment, the intention of the policy which is to be enforced by the PEP is that all communication flows destined to an endpoint associated with the Government should have the patient name field anonymised. In the present embodiment, anonymisation is implemented by replacing the personal identifiable values of the patient data (e.g. the name fields) replaced with a predetermined number of characters (x's in the present embodiment). With such an implementation of an anonymisation process, the enforcement mechanism for such a policy can deviate from the desired policy (i.e. it ca violate the policy) in several ways:

1. some messages may be anonymised correctly, whilst others may not be anonymised at all;
2. some messages may be anonymised correctly, whilst others may be anonymised incorrectly (e.g., just (the first) 3 characters are replaced by x's);
3. some messages may be anonymised incorrectly, whilst others may not be anonymised at all;
4. all messages may be anonymised, but with some faults or errors occurring (e.g., SOAP faults disrupt the flow of message processing);
5. frequent faults or errors may occur resulting for example in no messages being output at all;
6. incorrect anonymisation may be performed for every message
7. extra messages may be sent out which include patient data which should have been anonymised;

8. all messages may pass through unchanged, with no anonymisation; and
9. it may be that none of the messages are anonymised to the fixed length value ("xxxx") (i.e. some alternative change to the name fields may occur which may or may not result in some amount of anonymisation occurring).

Depending on the application, such policy violations can impact the system in different ways. If, for example, it is most important for the system that at least some anonymization should occur (and hence that the sensitive data is altered in some way before reaching endpoint E), then cases 2, 6, 7 and 9 are misbehaviors that are less critical than the other misbehaviors—such less critical misbehaviors may be considered to be merely misbehaviors whilst the other misbehaviors may be considered to be actual policy violations than violations. Either way, cases 1 to 9 listed above can be ordered by severity in different ways depending on the actual application and the specific policy requirements etc.

As described above, there are several ways in which a policy enforcement mechanism can act differently from the intention or objective of the policy. For enforcement indicators to be meaningful to the application administrator there are certain desired features of the enforcement indicators at the SOA message-level which are discussed below.

Two main properties that are desirable for policy enforcement assessment in a distributed application are accuracy and granularity. Firstly, an enforcement indicator should be able not only to correctly identify deviations, but also to accurately identify their features (e.g., types of faults and their context). For instance, anonymization deviations only apply to data that should be anonymized in the first place; the type of faults for cases 4 and 5 should be identified and captured along with the deviation, and also in case 9, whether anonymization happens on a fixed length. The preciseness of this detection should ideally be balanced with performance requirements, because assessment happens at runtime. Accuracy in identifying deviation depends on the amount of data analyzed at a time, the deviation description, and the average interval between deviations. Secondly, while indicator accuracy refers to the accuracy of deviation identification, granularity refers to the definition of the indicator: an enforcement indicator is fine-grained if it maps to one certain deviation type (e.g., looks just for case 9); conversely, an indicator is coarsely-grained if it aggregates several categories of misbehaviors (e.g., cases 1, 2, 3, 9 together, or an aggregation of both anonymization and encryption deviations). In order to have a correct enforcement indicator, its specification must define policy violations correctly. In order to infer how to define a violation, the present inventors investigated what a violation should not be. Examining cases 1-9 against a cause-effect model, they derived three desired properties of the execution of a security mechanism:

Correct Causes—Necessary Effects.

This refers to the property of an enforcement mechanism to produce desired effects for all triggering events (causes). For instance, every time the PEP 200 receives a message that contains patient data, the corresponding log will contain a record of that message having the patient data replaced with zeros or x-s.

Correct Causes—Sufficient Effects.

This refers to the property of an enforcer mechanism to produce only desired effects in the presence of triggers—i.e. the desired effects and no others. For instance, the only effect of receiving a message with patient data, is the same message with the patient data anonymized (and a log entry). Other unallowed effects can be calling other services or performing operations not required by the policy (e.g., case 7).

Robust.

This refers to the property of an enforcer mechanism to cope with faults. If a cause triggers a fault, then the policy should still apply on the data included in the fault. For instance, patient data included in the payload of a message that generated a SOAP fault should not be released as is, but should first be anonymised. Similarly any patient data included in a fault message (i.e. when generated as a result of a fault) should also be anonymised, etc.

For message-level policies, i.e. those that impose constraints on messages exchanged across the application infrastructure, the effects in the properties above translate to message flow patterns in the logged communication across services. By negating the first two properties above (intrinsically more vague compared to the third) for an environment that can analyze message traffic, the inventors have identified several possibilities of message sequences that can constitute allowed or, by negation, disallowed policy behavior as set out below:

(R1) absence/existence over a scope means a message or message flow should not trigger a message or message flow over that interval. For forbidden SOAP faults, this Maps to case 4.

(R2) universality over a scope means a message or message flow should happen for every time frame over the specified scope. Time frames are considered in order to be able to perform an online analysis. This maps to cases 9 and 6 above.

(R3) bounded existence over a scope means a message or message flow should trigger the wanted message(s) for a bounded number of times over the specified scope.

(R4) precedence over, a scope means a message or message flow should trigger a message only if preceded by another message (event) over the specified scope. In the anonymisation example, for example, there should not be a log entry without a sensitive message having caused that log entry being associated with it.

(R5) response over a scope means that a message or message flow should trigger a message (flow) that should then be followed by another one over the specified scope.

(R6) chain precedence over a scope means a message or message flow should trigger a message only if preceded by a certain chain of other messages over the specified scope.

(R7) chain response over a scope means a message or message flow should trigger an effect that should be followed by a certain chain of other messages over the specified scope.

With regards to scenarios where multiple policies are to be enforced, it may be that the effects that accompany correct enforcement are triggered by other policies. Overlapping enforcement events of multiple policies is outside the scope of the present invention; it is considered for purposes of the present application that in as much as the correct effect is triggered by a cause, the enforcement is correct.

In some embodiments of the present invention, deviations from the enforcement of a policy may be measured/determined in a three-step process: firstly by specifying violations and associated indicators in connection with the policy; secondly by instrumenting the enforcement implementation to obtain a trace that captures the relevant violations; and lastly by calculating the indicator measurement together with performing the corrections.

Policies are closely linked with indicators since the latter measure the implementation of a mechanism enforcing a policy, without knowing the details of such mechanism. It is realistic to consider that the policy creator has sufficient knowledge of the application constraints so that he or she can specify the most damaging unwanted behavior. For this reason, it is appropriate for the specification of an indicator to be included in a policy file. This inclusion can happen either, before or after the policy is written. Preferably the system includes a component to extract the indicator data and interpret it.

The indicator may in some embodiments take the form of a mathematical expression over a set of parameters that are policy deviations; the weights (or co-efficients) of the parameters may be included in the expression. Whether this expression is a linear combination of its parameters, or constitutes a more complicated mathematical relation, is an aspect that may depend on the application. The indicator expression may refer to violations, and each violation may have a type and its own parameters (e.g., an event that occurs all the time, sometimes, or never). The enforcement assessment system may compute violation occurrences at runtime, and with the indication parameters thus instantiated, may check if the indicator value exceeds a threshold; when it does, a handler of a certain correction type may be invoked.

Once the system has been instrumented to log messages that are relevant for the indicators calculation (hence to gather the deviations as soon as they happen, before being modified by any other entity), embodiments should process the log records. In some embodiments this analysis is done in realtime, as the system is running, in order to infer runtime indicator values and to use these to possibly be able react to the potential deviation in time (i.e. before a serious consequence occurs as a result of the violation instead of performing simply after the event diagnosis of a violation).

As it would be inefficient to analyze the logs every time a new log entry is added, a sliding-window technique may be used in some embodiments. In such a case a parameter t is defined such that only events that happened later than this time, t, are considered for analysis. In effect, a time window of duration t is slid over the log entries, and the window is advanced with the arrival of each new log entry.

It is also possible to save state from one computation of the indicator to the next. In other words, when a new value of some indicator is computed, access to the old value can still be provided. This allows for, in effect, the computation of indicators that depend on events outside of the sliding window, and in fact arbitrarily far back in time, should that be desired. Therefore the imposition of a sliding window is not a practical obstacle to computing indicators.

When events are logged at different points in the system, for example centrally in the message-level middleware, or at the service endpoints, it, is possible that log entries are produced out of causal order, causing an effect to appear in some logs earlier than its cause. This should obviously be taken into account when computing indicators. Equal care should be taken when analyzing log files that have been produced on different computers with different local clocks that may have changing offsets and drift. Synchronizing the machines involved using protocols such as NTP [10] should reduce the occurrence of this issue.

The next problem to tackle is to find those events that constitute (or are part of) a policy violation. As was argued in the introduction, it is easier to say that a certain outcome is undesired then it is to specify the system so that these undesirable outcomes are impossible by design: perfect precision, that is, unambiguous identification of policy-violating events, can be attained only with a perfect specification of the desired behavior of the system, and what log event sequences it can generate. Since it is assumed that the system does not possess precise specifications of the analyzed processes or whether an event violates a policy or not, methods are used which may unfortunately produce false positives (events classified as policy-violating when they are in fact not) and false negatives (events classified as not violating a policy when in fact they are). As long as such occurrences are rare they may not trigger an incorrect corrective behavior if an appropriate indicator threshold is set for example.

In the present anonymisation example, techniques from full-text searching are employed. The advantage of this is that a measure of the distance between the pattern and the match is obtained which enables a decision to be made on how heavily to weigh the match when updating an indicator, or whether to consider the match at all. The disadvantage is of course that there may be false positives and false negatives (as mentioned above).

The process of enforcing a policy is usually performed by a set of mechanisms: for instance, one that checks sender details for sender authentication, another mechanism that examines the message validity, and yet another one that analyses the message payload for sensitive data to be anonymised. With no knowledge of the flow among these mechanisms, little can be inferred about the actions of a PEP. Thus, for example, when a message is prevented by the PEP from reaching its destination it could for, example, be that a message was deemed illegitimate when its payload was not anonymised, but alternatively it could have been the result of some totally different cause—for example that the message was not well-formed, or that the sender could not be authenticated, etc. Knowing the input and/or output of at least one of these mechanisms allows to point more accurately to the mechanism in the enforcement implementation which may be a source of a violation.

In order to correct a violation it is advantageous to be able to pinpoint the source of the violation and enabling extra logging is one way to do that accurately. Specific branches or sequences of mechanisms in the implementation of the policy enforcement can thus be surrounded by instructions that produce finer-grained log entries about incoming and outgoing events (in the present example case, messages). This added information could contain the payloads of a message or messages (to enable for example the payload of an incoming message to be checked against the payload of a corresponding outgoing one); message metadata (to check where messages are directed to for example), or a message payload hash (to check if the payload has been modified at all without needing to know its actual contents). Apart from supplying finer-grained information about events inside the enforcement process without knowing its exact internals, this approach has the advantage of imposing the causal order over the logged events. That is, if mechanism M1 comes before mechanism M2 in the enforcement implementation, log entries of M1 will always come before those of M2, hence when the logging is done in one file, the output of M2 will always be logged after its cause (the input to M1).

In embodiments of the present invention, after the relevant deviations have been identified, a Decision Maker and Indicator State Updater corresponding to these components of FIG. 2 may compute a new value of the specified indicator, and compare it with a stated application-dependent threshold value. Corrective actions may come into play when the value of the indicator goes below (or above) the threshold. In the anonymisation example, for instance, a drop below 10% unanonymised messages might be interpreted as meaning that the mechanisms that perform anonymisation (rather than those that authenticate message sources or check message legitimacy) is not working correctly. Possible corrections in this case could be alerting the system administrator (usually the default is that the cause of the violation is not known) or replacing the faulty mechanism with another one (or redirecting all next messages to a trusted processor), etc.

An interesting associated problem is how to decide what is causing the indicator fluctuations, based on the indicator value and the events logged. This problem relies on correlating several elements:

- indicator value and most recent events: a sudden change in the indicator value, compared to values in the past, can reveal possibly severe deviations to have happened recently. If they are individual messages, they are easier to pinpoint than message flows that may have started long in the past;
- indicator fluctuations in time: can reveal if certain deviations happen repetitively at application runtime; with that clue, an administrator can investigate the causes of such deviations;
- indicator fluctuations and corrections: these can reveal if the performed corrective actions, are beneficent; i.e. have the desired effect over the system runtime.

While analysing these aspects can be of tremendous importance for security policy compliance and enforcement assessment, the basic process of root cause analysis is beyond the scope of this invention.

Following the above discussion of how indicators are calculated and how changes in their values lead to corrective actions being performed, this section describes how a specific corrective action is chosen. In embodiments of the invention, the actual corrective action that can be performed to correct the enforcement issue highlighted by an indicator may depend on the capabilities exposed by each system under question. The aim is to patch the misbehavior in a way that is most appropriate to the type of misbehavior. Thus, in essence the main abstract idea involved in the use of corrective actions is that of type flags to correlate the corrective actions with the indicators and changes in their values. This flag is associated with the property that an indicator is measuring: correctness of enforcement, robustness, or side-effects for example.

In a specific implementation of our invention, five types of indicators and related corrective actions are considered (as set out below), but the scope of the invention can be easily seen as bigger than the five mentioned below since the architecture may be agnostic to the specific indicators and actual corrections undertaken:

1. parameters: if the indicator is being calculated for a policy where parameters can be tuned and their actual tuning may be critical in correct enforcement, then the corrective actions may be used to adjust these parameters;
2. blocks: if the indicator is used to measure the correct working of a particular block of operation (or filter—see our discussion below of a specific example implementation of an embodiment of the present invention), the correction may be to either insert certain enforcement components before or after the particular block, or to modify or replace the block with another one;
3. chains of blocks: if the indicator is used for measuring a chain of blocks, then a corrective action may be to use another chain instead;
4. user/usage: if the indicator is used to identify a misbehaving user or unwanted usage, then the corrective action considered may be to ban the user or limit that activity; and
5. default: a generic indicator that is not captured by the above four types may lead to a default corrective action, e.g., a system specific alarm.

With the aim of providing flexibility in the corrective system, a design decision may be made not to have the corrective actions be always specified in the policy itself. This allows for various scenarios to be addressed by the system. For example, consider a scenario where the policy writer suggests a concrete correction C, but the action cannot be performed because C cannot be invoked for some reason. Knowing the type of the deviation and the corrective action required may be sufficient to allow a system to choose another corrective action in the place of C. In another instance, the policy writer may suggest a generic class of corrections C1 that depends on some criterion. The system may then be able to choose what exact corrective action to perform, from matching C1 with a type of correction that it knows it has. For example, the type (given explicitly when writing the indicator hints) is (type) "chain of block or filters" from (location) "start-block" to "end-block". The policy writer can then specify as correction—"authentication with Kerberos". This provides a tighter control over what's happening, with the type being specified explicitly.

To a large extent the decision on whether to specify the corrective actions in the policy depends on the type of actions. For example, in some cases, the policy writer may not know exactly what to do when the indicator value changes, say drops below 30%. In such cases, he can instruct the system to correct the problem by using a block of filters that does a certain type of action, say, call a method, which could internally analyse the situation and take more targeted action. This approach works with single filters, or blocks of filters, or alarms when the policy writer doesn't care about exactly what happens where. However, in the cases where the corrective actions are parameter adjustments, this approach may not work and the corrective action(s) may be specified in the policy as a piece of code that is interpreted and executed centrally.

Implementational Details of an Example Embodiment

As mentioned above, the example embodiment as described above with reference to FIGS. 1 to 3, was built using an out-of-the-box third party middleware tool produced by a company called Vordel—in particular, a Vordel XML gateway (see http://www.vordel.com/products/gateway/index.html) was used. The Vordel gateway is an XML gateway for Service Oriented Architecture (SOA)'s that offers processing of messages on the enterprise infrastructure by means of message-level policies. Such policies can be constructed by chaining prebuilt mechanisms in the desired process flow; the configuration of such mechanisms can be adjusted by the policy enforcement developer using software tools provided by Vordel.

In this example embodiment, patient records are captured in XML files or records. An extract from an example such XML record of a patient record prior to anonymisation is illustrated in FIG. 4. The same extract after anonymisation is illustrated in FIG. 5. It can be seen that the content of the XML fields tagged by the tags "lastname" and "firstname" have been changed from "Jones" and "Danny" respectively to "xxxxx".

Figure 6:
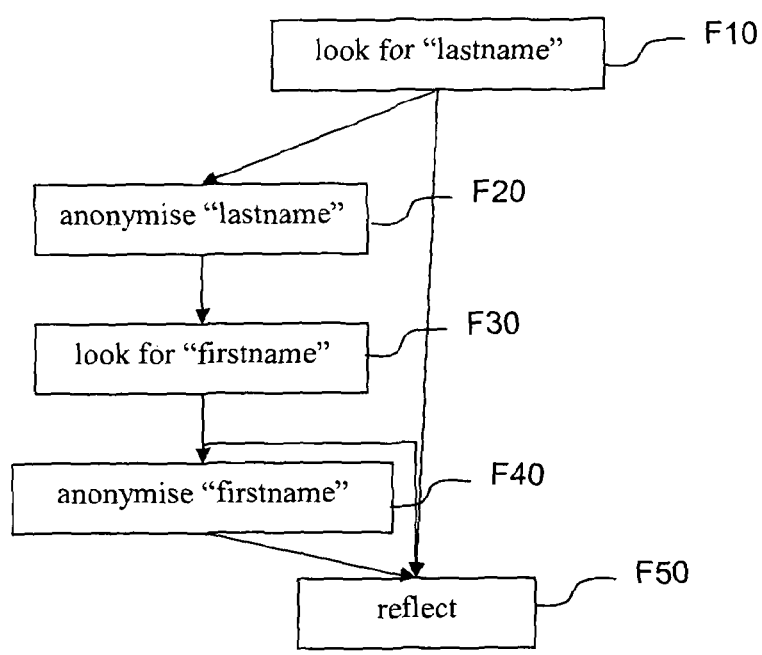
FIG. 6 is a schematic illustration of the Vordel enforcement blocks used to implement the anonymization function of the PEP of FIG. 2.

FIG. 6 shows an implementation of the PEP 200 to comply with the anonymisation policy (prior to its enhancement) prior to an administrator adding extra logging capabilities to make it appropriate for use in the present embodiment. The Vordel gateway and associated configuration software tools enable functionality within the gateway to be added by building a chain of blocks referred to as filters. In the present example the chain of filters used to implement the basic anonymisation function (prior to additional logging capabilities being added) comprises four filter blocks illustrated as a look for "lastname" filter F10, an anonymise "lastname" filter F20, a look for "firstname" filter F30 and an anonymise "firstname" filter F40. The chain is terminated in the standard manner in which chains of Vordel filter blocks are terminated with a so called reflect block F50 which simply returns the message processing to the stage which called the chain. As suggested by the names of the above filters, the look for "lastname" filter F10 inspects an input XML record (e.g. a SOAP message) and looks within it for a tag called "lastname", if it finds such a tag in the examined XML record it proceeds to the anonymise "lastname" filter F20 in which the content of the field tagged with "lastname" is modified to "xxxxx" and then the record is passed to the look for "firstname" filter F30. If no tag called "lastname" is identified by filter F10, then the record is, in this embodiment, passed straight to the reflect filter F50 (the assumption being that if no lastname tag is found no firstname tag will be found either). At the filter F30 a tag called "firstname" is searched for and if one is found the record is passed to the anonymise "firstname" filter F40 in which the content of the field tagged with "firstname" is modified to "xxxxx" and then the record is passed to the reflect filter F50. If no such tag is identified by filter F30 then filter F40 is bypassed and the record is passed directly to the reflect filter F50.

Thus, the implementation consists of several types of pre-built mechanisms that have been configured to implement together an anonymisation policy: the "Look for" filters of this process are decision blocks that examine an incoming XML message on the gateway and decide whether it matches the criterion of the filter or not (in this case, the presence of a node called lastname or firstname); the anonymise filters are message processors that internally replace a part of an XML message, with a given one (in this case, they replace the value of the fastname or firstname elements, with "xxxxx"). Since the condition that a filter checks against a message is boolean, a filter can have a green branch (condition evaluates to true) and a red branch (condition evaluates to false). In this way, all incoming traffic that the gateway intercepts passes sequentially through this box-and-arrows policy enforcement chain.

Figure 7:
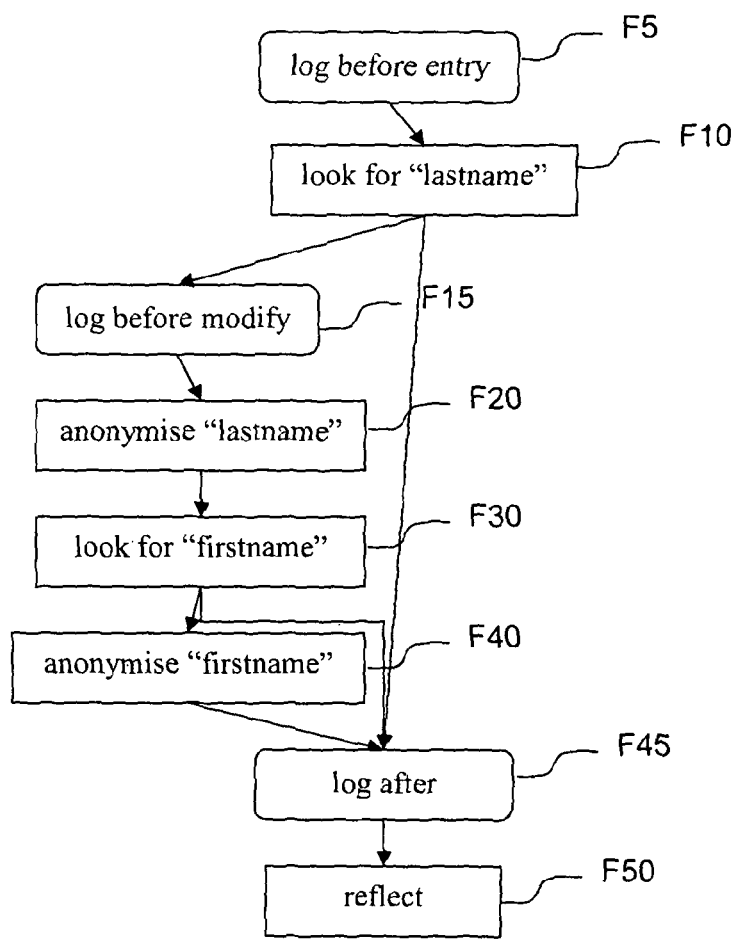
FIG. 7 is a schematic illustration of the Vordel enforcement blocks used to implement the anonymization function of the PEP of FIG. 2 after additional logging blocks have been added to enable the correctness of the PEP to be monitored.

FIG. 7 shows the same filter chain after it has been modified (in the present case by a human administrator). As can be seen the chain has been modified to include three extra logging filters: a log before entry filter F5, a log before modify filter F15 and a log after filter F45. As suggested by the names of these filters, they generate log records respectively as soon as the chain is called before it performs any processing (F5), after filter F10 has identified a tag called "lastname" but before the filter F20 is executed to modify the contents of the XML record being processed (F15) and at the end of the chain prior to the reflect filter F50 being invoked (F45).

The trace/log system 220 and log DB 300 uses the existing systems provided by the Vordel gateway and in general this type of functionality is expected to be present in most PEP systems in the market today.

The gateway logs events using its own XML schema: a log record contains log event metadata and log event payload, which is in fact the transferred SOAP message. An example extract of such a log record is shown in FIG. 8 from which it can be seen that the log event metadata (hereby called envelope) contains information about the log block that generated the message, the success of the operation, timestamp and message sender and receiver endpoints. In order to process the gateway logs, the Log Analyzer uses the XQuery query language. In order to identify the wanted violation patterns from the log records, the present embodiment uses a program which utilizes the Apache Lucene java API package for string matching. A provider of the features of these technologies is Berkeley Nux an open-source Java toolkit for XML processing, that is used in the present embodiment to form the log analyzer and decision maker functional modules 110 and 120.

The log analyser 110 and Decision Maker 120 of the present embodiment scan the logs as an XML stream and extracts the occurring violations in two stages: first, a filtering component—the Log Analyser—performs a search of potential violations (similar to filtering indicator related events) over the current time window; these potential violations are kept in store with all their metadata. In the present embodiment, the filter looks for messages with tags lastname and firstname, associated with a particular log filter (in particular the log after log filter F45 since logs from the earlier two need not contain anonymised data) using the query shown in FIG. 9. The XQuery query is stored in a String that is then executed by the Nux API with a query: execute( ) invocation; the query declares the SOAP namespace for the SOAP envelope data; then declares another namespace that depends on the schema of the Web service being invoked, and lastly searches with the envelope for a certain node. (In the present embodiment, all nodes within the record are searched but in an enhancement the identity of which nodes to filter may be based on data extracted from the indicator specification in a corresponding policy).

In the present embodiment, the Decision Maker 120 is implemented using a small modification to the XQuery of FIG. 9 as shown in FIG. 10. The main difference is that rather than just looking for records containing a lastname and firstname tag, it also inspects the contents of any such fields and performs a comparison of the contents with the expected string xxxxx. The distance of the contents from this expected value is expressed as a score which is passed to the indicator state updater 130.

The Decision Maker 120 in the present embodiment conducts a processing of the records found by the Log Analyser 110 to look for violations as specified in the policy. The records processed can be limited to those within a current time window, or not and a score for each such record which is processed is passed to an Indicator State Updater module 130 which takes these scores and updates a corresponding anonymisation policy indicator value in the manner described above. (In future embodiments, rather than being hardwired with a criteria specified by a human administrator as has been done in the present case as to what sort of comparison should be made, there could be an additional parameter input to the Decision Maker 120 parsed from the enhanced policy specifying what the data being compared should or should not look like—e.g. to specify that it should be an "xxxxx").

Apache Lucene, a cross-platform text search engine, is used within the Decision Maker of the present embodiment to search for exact or approximate matches. One of the features of Lucene is that of wrapping a query with a text match functionality, whereby the match of two text parameters is done based on a score; the score measures string distance and is a value between 0 and 1, where 0 means 'not matching' and 1 means 'exact match'. The internal algorithm for this metric is that of the Levenshtein distance between two strings—the minimum number of edits (character delete, insert or substitute) to transform one string into another. Based on Lucene, as integrated in the Nux API, the XQuery query becomes only slightly more complicated, as shown in FIG. 10. The lucene: match( ) call will invoke the approximate string match on the value of the patient data node in the SOAP envelope, with the anonymisation value, based on a given similarity score. By default the score is 0, meaning any approximations of the value "xxxx" are considered violations and hence added to the indicator value. But if, for instance, it is enough that "xxxx" be "xxx" followed by one more character, Lucene supports wild-card matching: xxx? for any character after the first three; xxxx*for any number of characters after "xxxx", or generically xxxx~0: 8 for a fuzzy match with a similarity score of 0.8.

In this way, using Apache Lucene and the expressive power of XQuery, the Decision Maker 120 of the present embodiment can extract all occurrences of unwanted node text where an approximation of the anonymised value should be. Counting such occurrences is given by default by XQuery, and the obtained number is given to a mathematical formula evaluator. This formula evaluator takes the expression of the indicator formula, and replaces the parameters with the counts of the matches returned by the query over the log. If the expression of an indicator has more than one parameter, there is no need to perform a new query: the original Log Analyser query can be enriched with new elements to search for in the same pass.

As the log messages produced were at the level of the filters, a design decision was made that the corrective action to be taken by the Correction Performer module 150 of the present embodiment would be to replace the anonymisation chain of filters in the event of any errors with an alternative previously configured chain of filters. Thus when the Decision Maker 120 notes that the indicator value has fallen below a predetermined threshold the correction evaluator module 140 is called and it calls the correction performer to perform a correction by replacing the current chain of filters with an alternative pre-built and pre-stored chain of filters (this approach envisages that if a new chain is configured to provide additional functionality the old less functional but trusted chain is stored and if the new chain proves unreliable in some way it can be automatically swapped out for the old trusted chain). In the present embodiment therefore, the correction evaluator does not do very much other than to call a single predetermined correction.

However, a very slightly more elaborate embodiment is envisioned in which the correction evaluator module does perform some more functionality. In this embodiment the correction evaluator when it has been notified by the Decision Maker that the indicator has fallen below the prespecified threshold it parses the log data to identify if just one of the anonymization filters appears to be at fault. Additionally, the correction performer 150 has pre-stored and available to it two different chains of filters in which just one of the anonymization filters F20 or F40 differs from the original filter chain. If the correction evaluator evaluates that just the lastname anonymization filter F20 is at fault it causes the pre-built chain in which just the lastname anonymization filter differs, etc. In other words, the correction evaluator evaluates the log data to try to identify exactly what kind of problem has occurred and to select an appropriate correction behavior etc.

In the specific embodiment of the invention using the Vordel system, the correction is performed using the APIs provided by the Vordel XML Gateway Management Web Service. These APIs allow for the management of the policy engine's filter ruleset.

Thus, in the slightly more elaborate version of the present embodiment, the Vordel XML Gateway is pre-equipped with various filter chains or rulesets, each using different blocks/components for anonymising the firstname and lastname elements. Each of these blocks have some difference in implementation and in a real-life situation could easily be components provided by various vendors. When the Decision Maker informs the correction evaluator module that a violation has occurred, the Correction Evaluator identifies the anonymisation block that is at fault and decides based on this evaluation which of the alternative filter rulesets would be appropriate.

Once the correction evaluator has determined a replacement filter chain to be used, it causes the correction performer to deploy that filter chain. In the present embodiment this is done by using the capability of the Vordel Gateway that is exposed as a web service. Once this new ruleset is deployed the gateway is restarted for the changes to take effect.

The pseudocode below shows how this is done by the Correction Performer in the present embodiment:

```
boolean resp1 =
    SetPolicyChain("Policy_AnonBlock_FirstName_Vendor2");
        // Argument is name of new policy chain
    if (resp1) {// proceed only if precious action was successful
        boolean resp2 = Restart("New Policy Set"); //Argument is string
            denoting reason for restart
```

In the specific case of the prototype implementation using the Vordel XML Gateway PEP, the above pseudocode can be mapped into the following Web Service calls:

```
boolean resp1 = setVordelPolicy("Policy_AnonBlock_
Vendor2.xml");
if (resp1){
    boolean resp2 = restartGateway(""); //No argument need in Vordel to
    restart
}
```

In summary therefore, the PEP enforcer 100 (which corresponds in the present embodiment to the claimed apparatus) comprises a monitor (which corresponds to the claimed monitoring component and which includes the Log Analyser 110, Decision Maker 120, the Indicator State Updater 130 and the Correction Evaluator 140) for monitoring the output of a policy controlled module (i.e. the PEP 200) operating within a distributed computer system and a correction performer 150. The PEP 200 is associated with one or more policies which are applied to the policy controlled module. Each policy specifies a trigger event or events and an action or actions to be performed as a result of the trigger event occurring, as well as expected output from the PEP when carrying out an action or actions specified in the policy. The monitor monitors output produced by the PEP 200 as a result of operating in compliance with a specified policy, and it compares the monitored output with the expected output as specified in the policy. The monitor (and in particular the correction evaluator) generates a request for corrective actions (to be taken by the correction performer 150) in the event that the comparison indicates a divergence between the expected and observed outputs. Finally, the correction performer 150 (which corresponds to the claimed correction component) then performs the requested corrective actions.

The invention claimed is:

1. An apparatus for use as a device within a distributed computing system, the distributed computer system comprising a plurality of devices interconnected by a data network, the interconnected devices being communicable with each other using messages transmitted over the data network, the apparatus comprising:
    a monitoring component and a correction component; and
    at least one processor configured to execute the monitoring component and the correction component,
        wherein the monitoring component is operable to monitor the output of a policy controlled device, the policy controlled device forming one of the devices of the distributed computer system, the policy controlled device being associated with one or more policies which are applied to the policy controlled device in order to control the behavior of the policy controlled device, each said applied policy specifying a trigger event or events and an action or actions to be performed by the policy controlled device as a result of the trigger event being detected as having occurred, the monitoring component being further operable to compare the monitored output with one or more specified expected outputs and to generate a correction request in the event that the comparison indicates a divergence between the expected and observed outputs;

wherein the correction component is operable to perform corrective actions as specified in the correction request generated by the monitoring component; and wherein each said applied policy further specifies the expected outputs with which the monitored output is compared by the monitor.

2. The apparatus according to claim 1, wherein:
the monitored output includes log data; and
the monitoring component includes a log analyzer for analyzing the log data.

3. The apparatus according to claim 1, wherein the correction component includes means for modifying the policy controlled device or the behavior thereof, including replacing the policy controlled device in question, without modifying a policy applied to the policy controlled device.

4. The apparatus according to claim 1, wherein the monitoring component includes an indicator value updater for updating an indicator value based on the comparison of the monitored output with the expected output and a decision maker for monitoring the indicator value and determining whether a pre-specified condition associated with the indicator value is satisfied.

5. A method of operating a distributed computer system, which comprises a plurality of devices interconnected by a data network, the interconnected devices being communicable with each other using messages transmitted over the data network, the distributed computer system including a policy controlled device whose behavior is at least partly specified by one or more policies, each of the one or more policies specifying a trigger event or events and an action or actions to be performed by the policy controlled device in response to a trigger event being detected, and wherein each policy additionally specifies expected output from the policy controlled device, the method comprising:

comparing the output from the policy controlled device with the expected output specified in a policy; and performing corrective actions in the event that the comparison indicates a difference between the monitored output and the expected output, wherein each applied policy further specifies the expected outputs with which the monitored output is compared by the monitor.

6. The method according to claim 5, wherein the monitored output includes log data and further comprising monitoring the output log data.

7. The method according to claim 5, wherein performing corrective actions comprises modifying the output of, or the input to, the policy controlled device or the behavior thereof, without modifying a policy applied to the policy controlled device.

8. The method according to claim 5, further comprising:
updating an indicator value based on the comparison of the monitored output with the expected output,
monitoring the indicator value, and
determining whether a pre-specified condition associated with the indicator value is satisfied.

9. A non-transitory computer readable storage medium including executable instructions programmed to cause a processor, when executing the instructions, to carry out the method of claim 5.

10. An apparatus for use as a device within a distributed computing system, the distributed computer system comprising a plurality of devices interconnected by a data network, the interconnected devices being communicable with each other using messages transmitted over the data network, the apparatus comprising:

a communication circuit; and at least one processor and memory coupled thereto;

wherein the at least one processor and the communication circuit are configured to cooperate with one another to enable the apparatus to interface with at least the data network, the at least one processor being further configured to control the apparatus to at least execute functionality comprising:

monitoring the output of a policy controlled device, the policy controlled device forming one of the devices of the distributed computer system, the policy controlled device being associated with one or more policies applied to the policy controlled device in order to control the behavior of the policy controlled device, each said applied policy specifying a trigger event or events and an action or actions to be performed by the policy controlled device as a result of the trigger event being detected as having occurred;

comparing the monitored output with one or more specified expected outputs;

generating a correction request in the event that the comparison indicates a divergence between the expected and observed outputs; and causing performance of corrective actions, as specified in the generated correction request; and wherein each said applied policy further specifies the expected outputs with which the monitored output is compared by the monitor.

11. The apparatus according to claim 10, wherein the monitored output includes log data, and wherein the log data; the at least one processor being configured to control the apparatus to execute further functionality comprising analyzing the log data.

12. The apparatus according to claim 10, wherein the at least one processor is configured to control the apparatus to execute further functionality comprising modifying the policy controlled device or the behavior thereof, including replacing the policy controlled device in question, without modifying a policy applied to the policy controlled device.

13. The apparatus according to claim 10, wherein the at least one processor is configured to control the apparatus to execute further functionality comprising:

updating an indicator value based on the comparison of the monitored output with the expected output; and monitoring the indicator value and determining whether a pre-specified condition associated with the indicator value is satisfied.

* * * * *